(12) United States Patent
Kübler et al.

(10) Patent No.: US 7,947,009 B2
(45) Date of Patent: May 24, 2011

(54) SURGICAL SYSTEM AND METHOD FOR CONTROLLING FLUID WHEN TREATING A CATARACT WITH THE PHACOEMULSIFICATION TECHNIQUE

(75) Inventors: Christoph Kübler, Oberkochen (DE); Michael Eichler, Essingen (DE); Tobias Maier, Aalen (DE)

(73) Assignee: Carl Zeiss Surgical GmbH, Oberkochen (DE)

( * ) Notice: Subject to any disclaimer, the term of this patent is extended or adjusted under 35 U.S.C. 154(b) by 0 days.

(21) Appl. No.: 11/898,091

(22) Filed: Sep. 10, 2007

(65) Prior Publication Data

US 2008/0082040 A1    Apr. 3, 2008

(30) Foreign Application Priority Data

Sep. 8, 2006   (DE) .......................... 10 2006 042 815
Nov. 17, 2006  (DE) .......................... 10 2006 054 628

(51) Int. Cl.
    *A61M 1/00*       (2006.01)
(52) U.S. Cl. ............................. 604/27; 604/30; 604/118
(58) Field of Classification Search .................. 604/118, 604/119, 30
    See application file for complete search history.

(56) References Cited

U.S. PATENT DOCUMENTS

| | | | | |
|---|---|---|---|---|
| 3,589,363 | A | * | 6/1971 | Banko et al. ..................... 604/22 |
| 4,136,678 | A | * | 1/1979 | Beach .............................. 604/19 |
| 4,475,904 | A | * | 10/1984 | Wang ............................ 604/119 |
| 4,496,342 | A | * | 1/1985 | Banko ............................. 604/27 |
| 4,832,685 | A | | 5/1989 | Haines |
| 5,200,430 | A | * | 4/1993 | Federman ..................... 514/772 |
| 5,697,898 | A | | 12/1997 | Devine |
| 6,261,283 | B1 | | 7/2001 | Morgan et al. |
| 6,740,074 | B2 | | 5/2004 | Morgan et al. |
| 6,908,451 | B2 | * | 6/2005 | Brody et al. .................. 604/118 |

* cited by examiner

*Primary Examiner* — Kevin C Sirmons
*Assistant Examiner* — Brandy C Scott
(74) *Attorney, Agent, or Firm* — Walter Ottesen

(57) ABSTRACT

A surgical system controls a fluid and includes an irrigation line and a first fluid vessel for holding the irrigation fluid. The irrigation line connects the first fluid vessel to a handpiece. An aspiration input line connects a suction pump to the surgical handpiece and permits the suction pump to draw fluid through the surgical handpiece. A pressure sensor detects the pressure of the fluid in the aspiration input line. An aspiration output line connects the suction pump to a collection vessel to permit fluid from the suction pump to be conducted into the collection vessel. A second fluid vessel accommodates irrigation fluid therein and an aspiration ventilation line connects the second fluid vessel to the aspiration input line. A venting valve in the aspiration ventilation line is switchable in dependence upon the fluid pressure in the aspiration input line.

16 Claims, 4 Drawing Sheets

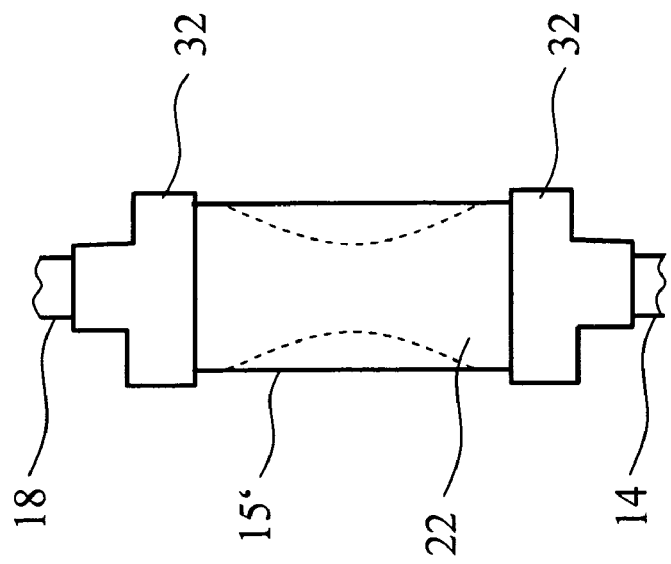
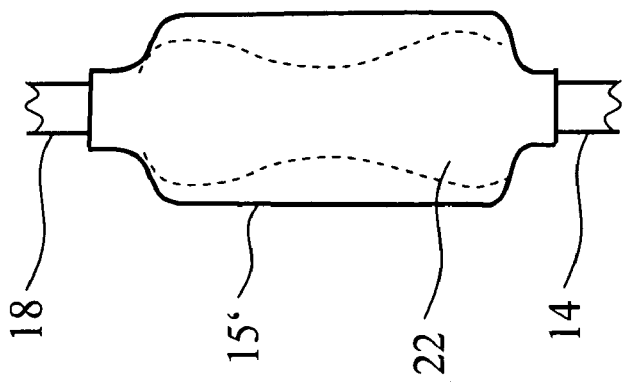
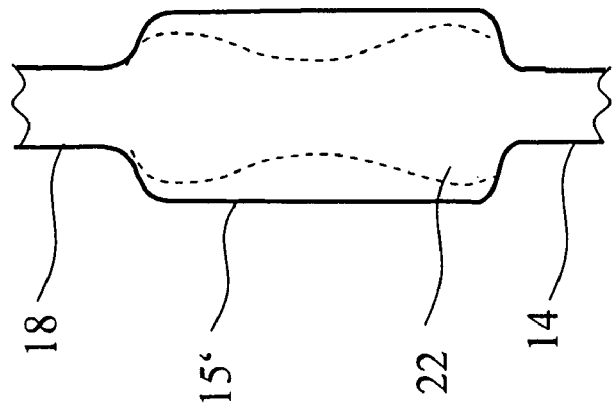

SURGICAL SYSTEM AND METHOD FOR CONTROLLING FLUID WHEN TREATING A CATARACT WITH THE PHACOEMULSIFICATION TECHNIQUE

CROSS REFERENCE TO RELATED APPLICATIONS

This application claims priority of German patent application nos. 10 2006 042 815.3 and 10 2006 054 628.8, filed Sep. 8, 2006 and Nov. 17, 2006, respectively, the entire contents of which are incorporated herein by reference.

FIELD OF THE INVENTION

The invention relates to a surgical system and a method for controlling fluid when treating a cataract with the phacoemulsification technique.

BACKGROUND OF THE INVENTION

A clouding of the lens is referred to in medicine as a cataract. Several surgical techniques are available for treating a clouding of the lens. The most widely used technique is phacoemulsification wherein a thin tip is introduced into the sick lens and is excited to vibration with ultrasound. In its immediate vicinity, the vibrating tip emulsifies the lens in such a manner that resulting lens fragments are drawn off by a pump through a line. When the lens has been completely emulsified, then a new artificial lens can be seated in the empty lens capsule so that a patient treated in this manner can again obtain good vision.

In phacoemulsification, a device is used which generally comprises: a vibration-capable tip in a handpiece, an irrigation line for the supply of irrigation fluid to the lens to be treated and an aspiration line for transporting away emulsified lens fragments into a collection vessel. It can happen that a lens fragment clogs the input region of the handpiece tip during the transport away into the collection vessel. A vacuum builds up downstream in the aspiration line when a suction pump runs continuously. For example, because of continuous ultrasonic vibrations of the tip, the lens fragment can break into smaller segments whereby an occlusion is abruptly ended. The built-up underpressure in the aspiration line leads to the situation that a relatively large quantity of fluid is drawn by suction from the eye in a very short time when such an occlusion break-up occurs. This can cause a collapse of the anterior chamber of the eye. It is possible that the lens capsule is pulled to the tip of the handpiece and is penetrated by the tip. In addition to such an injury to the lens capsule, a tip which penetrates too deeply can cause damage of the vitreous body of the eye lying behind the lens capsule.

Various solutions are suggested in the state of the art in order to prevent a collapse of the anterior chamber of the eye after an occlusion break-up. In U.S. Pat. No. 4,832,685, the aspiration line can be connected to the irrigation line so that a pressure compensation is achieved via the irrigation fluid. Here it is disadvantageous that the fluid, which is present in the irrigation line, is excited to pressure fluctuations. This leads to an additional destabilization of the pressure in the anterior chamber of the eye. A further disadvantage is that contaminated fluid from the aspiration line can flow into the irrigation line when there is a fluid compensation of this kind. For this reason, such a surgical system can be used only for a single patient.

Another possibility comprises carrying out a pressure compensation by means of ambient air. Here, air at atmospheric pressure is introduced into the aspiration line. It is advantageous in this context that no excitation of a pressure fluctuation occurs in the irrigation line. The air, which is introduced into the aspiration line, however, changes the fluid characteristics of the induction system so that the air must be pumped out of the aspiration line in order to again obtain a dynamic suction pressure characteristic line in the aspiration line.

U.S. Pat. Nos. 6,740,074 and 6,261,283 are incorporated by reference and suggest taking fluid out of a collection vessel and to introduce this fluid into the aspiration line with the collection vessel being mounted at the end of the aspiration line. However, with this solution, contaminated particles from the collection vessel are introduced into the aspiration line so that such a system becomes unsterile and is not suitable for several patients but only for a single patient.

SUMMARY OF THE INVENTION

In view of the above, it is an object of the invention to provide a surgical system wherein a rapid pressure compensation is made possible when there is an underpressure in the aspiration line and wherein: no pressure fluctuations are introduced into the irrigation line; the fluid characteristics in the aspiration line are not changed; and, no contaminated fluid reaches the irrigation line so that the system can be used for several patients. It is also an object of the invention to provide a method for operating a surgical system of this kind.

The surgical system of the invention is for controlling a fluid. The surgical system includes: an irrigation line for conducting an irrigation fluid; a first fluid vessel for holding the irrigation fluid; a surgical handpiece; the irrigation line having a first end connected to the first fluid vessel and a second end connected to the handpiece; a suction pump having an inlet and an outlet; an aspiration input line arranged between the inlet of the suction pump and the surgical handpiece so as to permit the suction pump to draw fluid through the surgical handpiece; a pressure sensor for detecting the pressure of the fluid in the aspiration input line; a collection vessel; an aspiration output line connecting the outlet of the suction pump to the collection vessel so as to permit fluid from the outlet of the suction pump to be conducted into the collection vessel; a second fluid vessel for accommodating irrigation fluid therein; an aspiration ventilation line for connecting the second fluid vessel to the aspiration input line; and, a venting valve provided in the aspiration ventilation line and the venting valve being switchable in dependence upon the fluid pressure in the aspiration ventilation line.

With an occlusion in the aspiration line, fluid can be conducted out of the second fluid vessel and through the aspiration ventilation line into the aspiration input line in the system according to the invention. If, for example, after an occlusion break-up, the vacuum pressure in the aspiration line again increases in a direction toward normal suction pressure, then the ventilation line can be correspondingly switched to clear by the ventilation valve so that a rapid pressure compensation is possible and a drop of the suction pressure to a value which is too high is avoided. The supplied fluid does not originate from the first fluid vessel which contains the irrigation fluid and is connected to the irrigation line. A complete separation from this first fluid vessel is achieved via the second fluid vessel so that during the venting no pressure fluctuations can be excited in the irrigation line. Furthermore, a contamination of the irrigation line is entirely precluded by the separation of the two fluid vessels. Since the second fluid vessel contains sterile fluid, a contamination of the aspiration line by the venting is likewise precluded. In this way, it is possible that the surgical system can be used with several patients which are treated sequentially without the danger of a contamination because of previously introduced contaminants.

According to a preferred embodiment of the invention, the second fluid vessel can be filled via a fill line which has a filling valve. The fill line is connected at one end thereof to the irrigation line. In this way, it is sufficient to only fill the first fluid vessel with irrigation fluid so that, thereafter, the second fluid vessel can be filled from this sterile fluid. Such a filling of the second fluid vessel can, for example, take place before the start of a surgical procedure. With the fill valve, a reliable separation is obtained between the irrigation line and the portion of the fill line which faces toward the second fluid vessel. Preferably, the other end of the fill line ends at a predetermined distance to a maximum fluid level elevation of the second fluid vessel so that no direct touching contact is present between the other end of the fill line and the fluid in the second fluid vessel. In this way, a contamination of the irrigation line is precluded with still greater reliability.

If a sensor for detecting the fluid level in the second fluid vessel is provided, then a reduction of the fluid level can be detected after a venting of the aspiration input line and a refilling of the second fluid vessel can be started at a suitable time point. To increase the safety during refilling, the second fluid vessel can be connected to an overflow line through which excess fluid is conducted away into an additional vessel.

If the irrigation line and the aspiration line as well as the fluid vessel are used only for one patient each time, the danger of a contamination of the second fluid vessel is less so that, in another embodiment, it can be provided that the fill line at the other end thereof is connected to the second fluid vessel. Such a connection between the other end and the second fluid vessel is achievable via mechanical or chemical connecting means or via a thermal connecting method. For example, the connection can be via clamping, adhesive, welding and especially with plastics via a connection by means of polymerization or polycondensation.

A closed system can be formed when the fill line is connected to the second fluid vessel. When the fluid is drained from the second fluid vessel, then a pressure compensation must take place within the second fluid vessel. According to a preferred feature of the invention, this is achieved in that the second fluid vessel has a wall having at least one elastic deformable region. The reduction of the fluid quantity within the second fluid vessel then leads to a deformation of the elastic region so that no pressurized air or the like need be added to the second fluid vessel. In this way, the system can be operated in a relatively simple manner.

Preferably, the second fluid vessel is configured to have a tubular shape, for example, as a hose such as the fill line or aspiration ventilation line whereby a cost effective and easily realizable solution is achieved. The hose further affords the advantage that it is elastically deformable not only in a limited region but along its entire periphery. It is especially preferable to configure the fill line, the second fluid vessel and the aspiration ventilation line as one piece so that a simple assembly in a cassette is achieved.

When the irrigation line has an irrigation valve, the irrigation valve can be brought into such a position that the irrigation line is interrupted. A filling of the second fluid vessel with fluid from the first fluid vessel can be especially practically carried out by means of the fill line when the irrigation valve is arranged in the irrigation line between the handpiece and the fill line. In this case, when filling the second fluid vessel, no pressure fluctuations occur in the part of the irrigation line which is mounted between the irrigation valve and the handpiece. In this way, it is ensured that no pressure fluctuations are induced in the eye during filling of the second fluid vessel.

According to a further embodiment of the invention, the fluid can be conducted away from the aspiration ventilation line at the base or in the proximity of the base of the second fluid vessel. This ensures that the maximum available quantity of ventilating fluid can always be made available and, in addition, that no air is supplied into the aspiration input line when the vessel is filled.

Preferably, the pressure sensor detects the fluid pressure in the aspiration line close to the handpiece. In this way, when there is an occlusion break-up, it is possible that the pressure change is quickly detected because of the short path distance from the handpiece tip to the pressure sensor and therefore a drive of the ventilation valve can take place rapidly. A ventilation is achievable especially rapidly when the pressure sensor detects the fluid pressure in the aspiration line within the handpiece, preferably, in the proximity of the tip of the handpiece.

The object of the invention is further achieved with a method for controlling fluid when venting an aspiration input line in a surgical system of the kind described above. An increase of the vacuum pressure in the aspiration input line is detected by the pressure sensor in the handpiece after an occlusion break-up and the venting valve is so switched that fluid from the second fluid vessel is conducted from the aspiration ventilation line to the aspiration input line.

BRIEF DESCRIPTION OF THE DRAWINGS

The invention will now be described with reference to the drawings wherein:

FIG. 3 is a schematic showing several fluid vessels in a surgical system according to the invention; and, FIG. 4 shows the course of pressure in the aspiration line of the surgical system of the invention as a function of time.

DESCRIPTION OF THE PREFERRED EMBODIMENTS OF THE INVENTION

Figure 1:
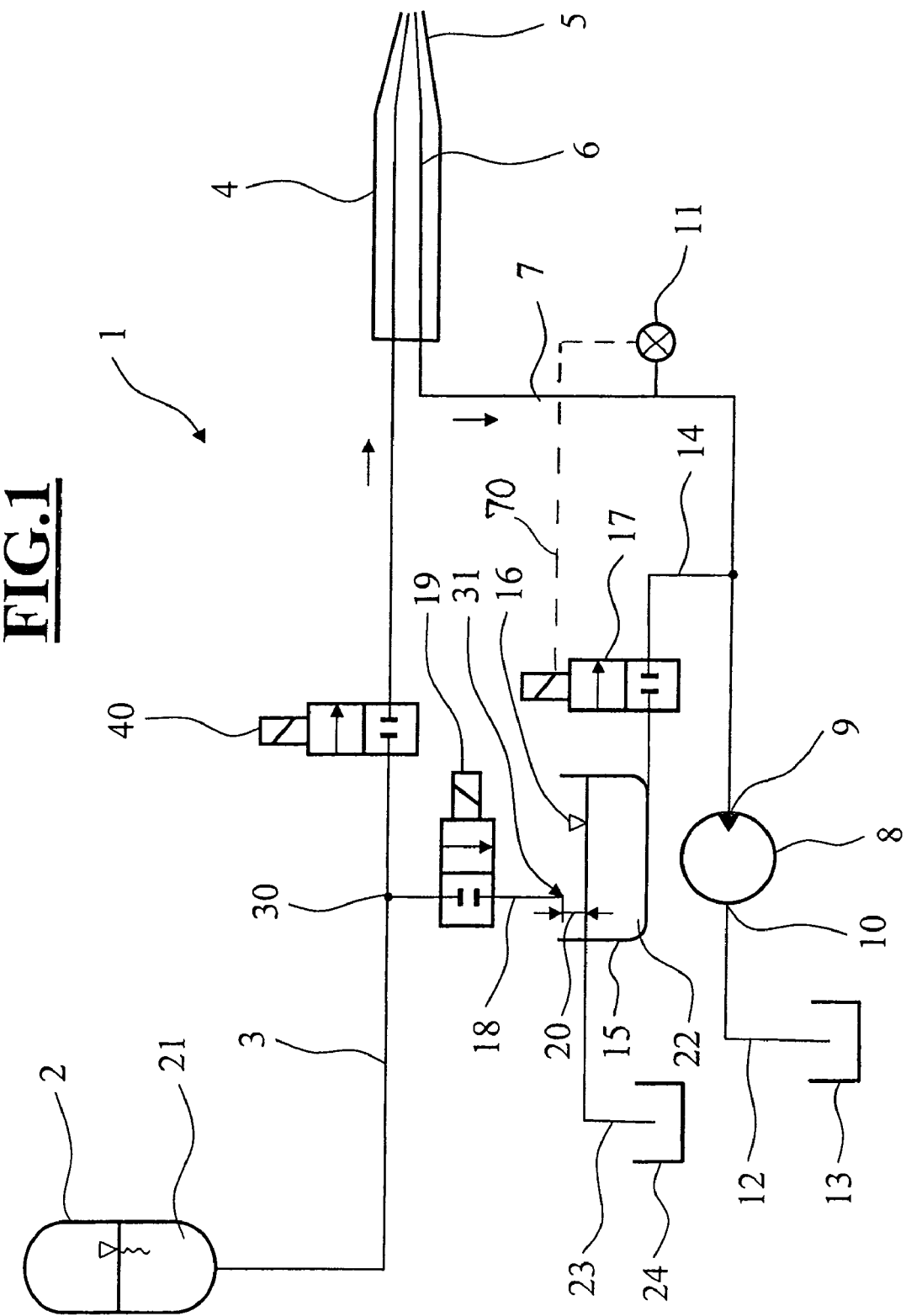
FIG. 1 is a schematic of a first embodiment of the surgical system according to the invention.

In FIG. 1, a schematic of an embodiment of the surgical system 1 of the invention is shown. An irrigation fluid 21 is held in a first fluid vessel 2 and this irrigation fluid can be guided via an irrigation line 3 to a surgical handpiece 4. The handpiece 4 can be a handpiece for phacoemulsification wherein a vibrating tip 5 emulsifies a clouded lens of an eye and the broken up lens fragments are drawn away by suction. An irrigation valve 40 is shown in FIG. 1 as a two-way valve and permits a passthrough or blocking of the irrigation fluid in a direction to the handpiece 4. An aspiration line 6 runs from the tip 5 to an end of the handpiece 4 in order to transport away emulsified lens pieces and fluid from the eye. The removal is caused by a suction pump 8 which is connected at its input 9 via an aspiration input line 7 to the handpiece 4. A fluid pressure in the aspiration input line 7 is detected by a pressure sensor 11 which is mounted between the input 9 of the suction pump 8 and the handpiece 4. Preferably, the pressure sensor 11 is disposed in the proximity of the handpiece 4 so that a pressure change in the region of the tip 5 can be detected after a short path distance through the handpiece 4. A still more rapid detection of a pressure change is achieved when the pressure sensor 11 detects the fluid pressure in the aspiration line 6 within the handpiece 4. In this case, the aspiration line 6 can be understood to be the forward section of the aspiration input line 7.

The suction pump 8 conducts the lens fragments and fluid at its output through an aspiration output line 12 into a collection vessel 13.

Figure 2:
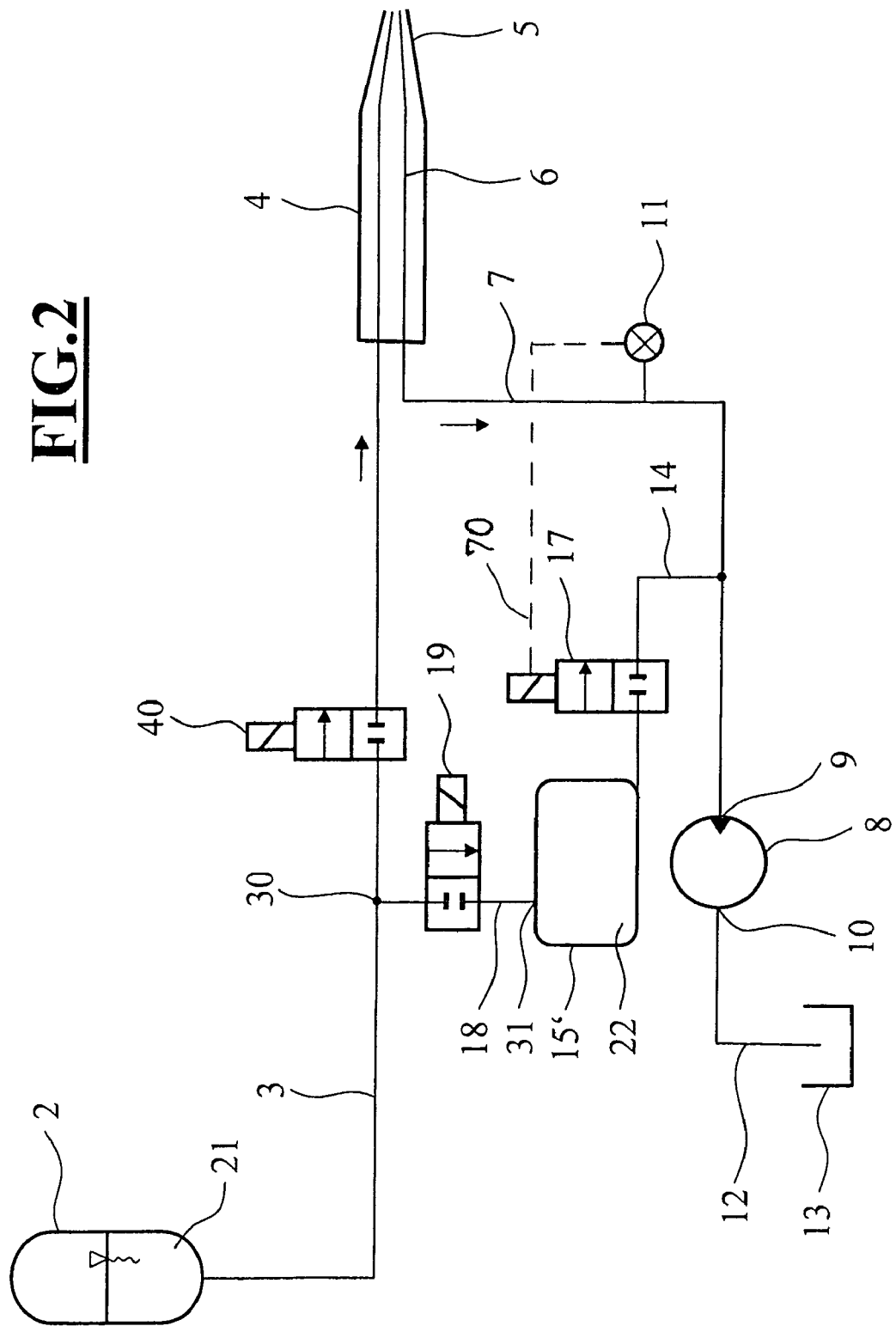
FIG. 2 is a schematic of a second embodiment of the surgical system according to the invention.

An aspiration ventilation line 14 is connected to the aspiration input line 7 and this aspiration ventilation line is connected to a second fluid vessel 15. In the second fluid vessel 15, a fluid 22 is contained which can be supplied into the aspiration input line 7 with a corresponding position of a two-way venting valve 17 provided in the aspiration ventilation line 14. If a clogging (occlusion) occurs because of lens fragments within the aspiration lines 6 or 7 which are too large, for example, at the distal end of the aspiration line in the region of the tip 5, so that a suction through the aspiration lines 6 and 7 is blocked, then a vacuum pressure builds up in these lines 6 and 7. This pressure can be detected by the pressure sensor 11. When the occlusion breaks up, the pressure in the line 7 increases from the vacuum pressure again in a direction toward atmospheric pressure. With this pressure change, a collapse of the eye anterior chamber can occur. To prevent this, and immediately after detecting the pressure change by the pressure sensor 11, the venting valve 17 is so driven and switched by an electronic circuit that fluid 22 from the second fluid vessel 15 is conducted into the aspiration ventilation line 14 and there into the aspiration input line 7. In FIGS. 1 and 2, the driving of the venting valve 17 is shown schematically by a broken line representing a signal line 70 between the pressure sensor 11 and the venting valve 17. An increase of pressure in the aspiration input line 7 which is too high is thereby prevented.

The second fluid vessel 15 is filled with a fluid 22 which can be supplied via a fill line 18 in the embodiment shown in FIG. 1. A two-way fill valve 19 is provided in the fill line 18 and blocks the passthrough of fluid or clears the fluid for passthrough. The fill line 18 is connected at one end 30 thereof to the irrigation line 3 so that fluid 21 can be supplied into the fill line 18. The other end 31 of the fill line 18 ends at a predetermined distance 20 from the maximum fluid level of the second fluid vessel 15 so that no direct touching contact is present between the other end 31 of the fill line 18 and the fluid 22 in the second fluid vessel 15. In this way, a complete separation is present between the irrigation line 3 and the second fluid vessel 15, that is, between the irrigation line 3 and the aspiration ventilation line 14 and the aspiration input line 7. A contamination of unsterile fluid in the aspiration input line 7 into the irrigation line 3 is thereby precluded also for a through switched filling valve 19.

One can do without a filling line 18 and a filling valve 19 so that the second fluid vessel 15 is a closed vessel like the first fluid vessel 2.

The second fluid vessel 15 is provided with a sensor 16 with which the fluid level can be detected in the second fluid vessel 15. With the sensor 16, it is ensured that the filling of the second fluid vessel 15 takes place only up to reaching the maximum permissible fluid level. The fluid vessel 15 has an overflow with an overflow line 23 to provide an additional measure of safety. Excess fluid can be conducted through the overflow line 23 into a vessel 24. The vessels 24 and 13 can be configured as one piece.

In the second embodiment of the surgical system shown in FIG. 2, the second fluid vessel 15' is a closed vessel. The other end 31 of the fill line 18 is connected to the second fluid vessel 15'. To make possible an emptying of the second fluid vessel 15', a pressure compensation within the vessel must be provided. This can be achieved, for example, in that a wall of the second fluid vessel 15' is provided with at least one elastically deformable region. The elastically deformable region can be a flexible cover on a rigid fluid vessel 15' or a flexible side wall. Furthermore, it is possible that the entire second fluid vessel 15' is configured to be elastically deformable, for example, as a hose or bag. When, after switching the venting valve 17 into an open position, the fluid 22 from the second fluid vessel 15' is transported into the aspiration ventilation line 14, the elastically deformable region of the second fluid vessel 15' pulls together whereby the fluid volume within the second fluid vessel 15' is reduced. The second fluid vessel 15' can again be filled completely with fluid 22 by closing the venting valve 17 and then opening the fill valve 19.

The second embodiment of the surgical system shown in FIG. 2 distinguishes from the first embodiment shown in FIG. 1, inter alia, in that a pressure compensation is not required for the second fluid vessel 15', for example, via atmospheric pressure. Furthermore, the sensor 16 for monitoring the fill level is not needed as provided in the first embodiment of the surgical system shown in FIG. 1. This applies also for the overflow line 23 for conducting away excess fluid into the vessel 24.

In FIG. 3, several forms of a fluid vessel 15' having at least one elastic deformable region are shown. The fluid vessels 15' are configured to have a hose shape and a direct connection to the fill line 18 and the ventilation line 14. The connection can be achieved via mechanical connecting means or chemical connecting means or via a thermal connecting process. In the form shown in FIG. 3A, the fill line 18, the second fluid vessel 15' and the ventilation line 14 are configured as one piece. The fluid vessel 15' thereby defines a mid section of the lines 18 and 14 which is expanded in diameter. In the form shown in FIG. 3B, the second fluid vessel 15' is a hose piece having tapered diameters at the ends which are connected to lines 18 and 14; whereas, in the form shown in FIG. 3C, an additional hose having corresponding reducing pieces 32 is provided. The manufacture of the fluid vessels 15' can, for example, take place via extrusion, blow molding or an injection molding process.

When fluid 22 is conducted away into the ventilation line 14, then for a closed fluid vessel 15' according to the second embodiment, the diameter in the center region decreases in each case as shown by the broken lines in FIGS. 3A to 3C.

When an occlusion is broken up, an increase of the vacuum pressure in the direction of atmospheric pressure is detected in the aspiration input line 7 by pressure sensor 11. Thereafter, the venting valve 17 is moved into a position so that the aspiration venting line is cleared and fluid 22 can be conducted from the second fluid vessel (15, 15') to the aspiration input line 7.

Figure 4:
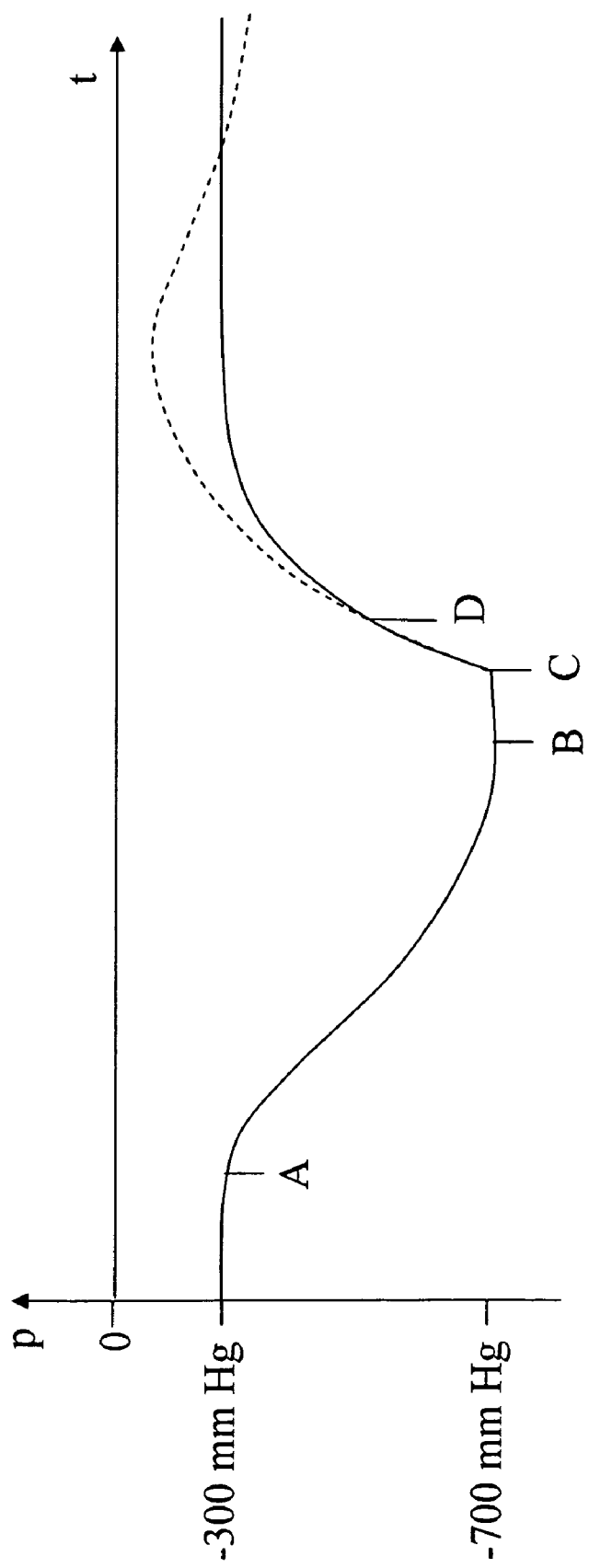

The effect of this venting operation is shown in FIG. 4 by means of a graph. The diagram shows a pressure course in an aspiration line 6 or 7 as a function of time. The suction pressure in the aspiration line increases continuously after the occurrence of an occlusion (event A) from the usual suction pressure in the amount of approximately −300 mm Hg until a maximum vacuum pressure is reached (event B). When the occlusion breaks up (event C), the vacuum pressure decreases again in a short time in a direction toward the usual suction pressure. This pressure change is detected shortly thereafter by means of the pressure sensor 11 (event D) so that the irrigation valve 40 and the venting valve 17 are correspondingly switched in order to achieve a filling of the aspiration input line 7. In lieu of a change of the vacuum pressure to values close to the atmospheric pressure (see broken line course in FIG. 4) as is still the case in the state of the art, a drop of the vacuum pressure only to the usual suction pressure of approximately −300 mm Hg is obtained because of the filling of the aspiration input line by the system of the invention. The filling can take place in such a manner that the pressure has already, reached the usual suction pressure of −300 mm Hg after less than 100 ms and, for a suitable placement of the pressure sensor in the vicinity of the tip 5 of the handpiece, the usual pressure of −300 mm Hg is reached already after 30 ms.

It is understood that the foregoing description is that of the preferred embodiments of the invention and that various changes and modifications may be made thereto without departing from the spirit and scope of the invention as defined in the appended claims.

What is claimed is:

1. A surgical system for controlling a fluid, the surgical system comprising:
    an irrigation line for conducting a sterile irrigation fluid;
    a first fluid vessel for holding the sterile irrigation fluid;
    a surgical handpiece;
    said irrigation line having a first end connected to said first fluid vessel and a second end connected to said handpiece;
    a suction pump having an inlet and an outlet;
    an aspiration input line arranged between said inlet of said suction pump and said surgical handpiece so as to permit said suction pump to draw aspirant fluid through and away from said surgical handpiece;
    a pressure sensor for detecting changes in pressure of the fluid flowing in said aspiration input line during aspiration of the fluid;
    a collection vessel for collecting said aspirant fluid;
    an aspiration output line connecting said outlet of said suction pump to said collection vessel so as to permit said aspirant fluid from said outlet of said suction pump to be conducted into said collection vessel;
    a second fluid vessel for accommodating only sterile irrigation fluid therein;
    an aspiration ventilation line for connecting said second fluid vessel to said aspiration input line;
    a venting valve provided in said aspiration ventilation line and said venting valve being switchable in dependence upon said changes in pressure of the fluid flowing in said aspiration input line so as to allow only sterile irrigation fluid from said second fluid vessel to flow from said second fluid vessel into said aspiration input line during said aspiration thereby causing only sterile irrigation fluid to prevent an unwanted drop in said pressure during a surgical procedure;
    a fill line for conducting sterile irrigation fluid to fill said second fluid vessel therewith;
    said fill line having a first end connected to said irrigation line; and,
    a fill valve disposed in said fill line for blocking and clearing the flow of fluid from said irrigation line through said fill line to said second fluid vessel.

2. A surgical system for controlling a fluid, the surgical system comprising:
    an irrigation line for conducting a sterile irrigation fluid;
    a first fluid vessel for holding the sterile irrigation fluid;
    a surgical handpiece;
    said irrigation line having a first end connected to said first fluid vessel and a second end connected to said handpiece;
    a suction pump having an inlet and an outlet;
    an aspiration input line arranged between said inlet of said suction pump and said surgical handpiece so as to permit said suction pump to draw aspirant fluid through and away from said surgical handpiece;
    a pressure sensor for detecting changes in pressure of the fluid flowing in said aspiration input line during aspiration of the fluid;
    a collection vessel for collecting said aspirant fluid;
    an aspiration output line connecting said outlet of said suction pump to said collection vessel so as to permit said aspirant fluid from said outlet of said suction pump to be conducted into said collection vessel;
    a second fluid vessel for accommodating only sterile irrigation fluid therein;
    an aspiration ventilation line for connecting said second fluid vessel to said aspiration input line;
    a venting valve provided in said aspiration ventilation line and said venting valve being switchable in dependence upon said changes in pressure of the fluid flowing in said aspiration input line so as to allow only sterile irrigation fluid from said second fluid vessel to flow from said second fluid vessel into said aspiration input line during said aspiration thereby causing only sterile irrigation fluid to prevent an unwanted drop in said pressure during a surgical procedure;
    a fill line for conducting sterile irrigation fluid to fill said second fluid vessel therewith;
    said fill line having a first end connected to said irrigation line;
    a fill valve disposed in said fill line for blocking and clearing the flow of fluid from said irrigation line through said fill line to said second fluid vessel;
    the fluid in said second fluid vessel having a maximum fluid level; and,
    said fill line having a second end terminating at a predetermined distance from said maximum fluid level so as to preclude a direct touching contact between said second end of said fill line and the fluid in said second fluid vessel.

3. The surgical system of claim 1, further comprising a sensor for detecting the fluid level in said second fluid vessel.

4. The surgical system of claim 1, further comprising an overflow vessel and an overflow line connected to said second fluid vessel for conducting excess fluid from said second fluid vessel to said overflow vessel.

5. The surgical system of claim 1, wherein said fill line has a second end connected to said second fluid vessel.

6. The surgical system of claim 5, wherein said second end of said fill line is connected to said second fluid vessel via mechanical or chemical connecting means or via a thermal connecting process.

7. The surgical system of claim 5, wherein said second fluid vessel has a wall with at least one elastically deformable region.

8. The surgical system of claim 5, wherein said second fluid vessel has a tube-like configuration.

9. The surgical system of claim 5, wherein said fill line, said second fluid vessel and said aspiration ventilation line are configured as a single piece.

10. The surgical system of claim 1, further comprising an irrigation valve mounted in said irrigation line.

11. The surgical system of claim 10, wherein said irrigation valve is mounted between said handpiece and said fill line.

12. The surgical system of claim 1, wherein said second fluid vessel has a base; and, said aspiration ventilation line conducts fluid from said second fluid vessel from a location thereon at or close to said base thereof.

13. The surgical system of claim 1, wherein said pressure sensor detects fluid pressure in said aspiration input line close to said surgical handpiece.

14. The surgical system of claim 1, wherein said pressure sensor detects fluid pressure in said aspiration input line within said surgical handpiece.

15. The surgical system of claim 1, wherein said surgical handpiece has a tip and said pressure sensor detects fluid pressure in said aspiration input line at the immediate vicinity of said tip.

16. A method for controlling fluid when venting an aspiration input line in a surgical system which includes: an irrigation line for conducting a sterile irrigation fluid; a first fluid vessel for holding the sterile irrigation fluid; a surgical handpiece wherein an occlusion can occur during a surgical procedure; said irrigation line having a first end connected to said first fluid vessel and a second end connected to said surgical handpiece; a suction pump having an inlet and an outlet; said aspiration input line being arranged between said inlet of said suction pump and said surgical handpiece so as to permit said suction pump to draw aspirant fluid through said surgical handpiece; a pressure sensor for detecting the pressure of the fluid in said aspiration input line; a collection vessel for collecting said aspirant fluid; an aspiration output line connecting said outlet of said suction pump to said collection vessel so as to permit said aspirant fluid from said outlet of said suction pump to be conducted into said collection vessel; a second fluid vessel for accommodating only sterile irrigation fluid therein; an aspiration ventilation line for connecting said second fluid vessel to said aspiration input line; and, a venting valve provided in said aspiration ventilation line and said venting valve being switchable in dependence upon the fluid pressure in said aspiration ventilation line; a fill line for conducting sterile irrigation fluid to fill said second fluid vessel therewith; said fill line having a first end connected to said irrigation line; and, a fill valve disposed in said fill line for blocking and clearing the flow of fluid from said irrigation line through said fill line to said second fluid vessel; the method comprising the steps of:

after a break-up of said occlusion in said surgical handpiece, detecting changes in pressure of the fluid flowing in said aspiration input line during aspiration;

switching said ventilation valve to allow only sterile irrigation fluid from said second fluid vessel to flow via said aspiration ventilation line to said aspiration input line during said aspiration thereby causing only sterile irrigation fluid to prevent an unwanted drop in said pressure during a surgical procedure; and, switching said fill valve to allow fluid from said irrigation line to pass into said second fluid vessel to thereby replenish the supply of irrigation fluid contained therein.

* * * * *